(12) United States Patent
Fang (10) Patent No.: US 8,626,467 B2
(45) Date of Patent: Jan. 7, 2014

(54) AIR POLLUTION SAMPLING SYSTEM AND METHOD THEREOF

(75) Inventor: Hsin-Fa Fang, Taoyuan County (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 936 days.

(21) Appl. No.: 12/761,661

(22) Filed: Apr. 16, 2010

(65) Prior Publication Data
US 2011/0257922 A1 Oct. 20, 2011

(51) Int. Cl.
*G06F 19/00* (2011.01)
(52) U.S. Cl.
USPC ............................................ 702/100
(58) Field of Classification Search
USPC ............................................ 702/100
See application file for complete search history.

(56) References Cited

PUBLICATIONS

Air Pollution Sampling and Analysis publish Date: May 2009 by Dr. Sharad Gokhale, 47 pages.*
Volkan Cevher, Vehicle Speed Estimation Using, Acoustic Wave Patterns, IEEE Transactions on Signal Processing, vol. 57, No. 1, Jan. 2009, p. 30-47.*

* cited by examiner

*Primary Examiner* — Tung S Lau
(74) *Attorney, Agent, or Firm* — Rosenberg, Klein & Lee (57) ABSTRACT

An air pollution sampling system and a method thereof applied to a wide-area air sampling are revealed. Air is forced into an air sampling unit by movement of a vehicle, for performing an active air sampling without a power source. An air sampling unit includes a plurality of baffle plates so as to adjust air sampling rate and avoid interference caused by turbulence generated during the movement of the vehicle. A positioning device provides geographic coordinates, vehicle speed and time. An information processing device integrates sampling flow and positioning information from the positioning device, collects information generated by the sampling system, and computes statistics of the accumulated samples and relative sampling positions. By the collected sampling positions, time and flow rate, the sampling amount is obtained through data processing and calculation. In combination with the display of positioning data, the geographic area represented by the air samples could be understood more clearly.

17 Claims, 5 Drawing Sheets

AIR POLLUTION SAMPLING SYSTEM AND METHOD THEREOF

BACKGROUND OF THE INVENTION

1. Fields of the Invention

The present invention relates to a air pollution sampling system, especially to an active air pollution sampling system that combines with positioning devices such as a GPS, INS/GPS or INS/GPS/AHRS, Wi-Fi positioning etc. It could sample in wide area without use of a power source.

2. Descriptions of Related Art

Monitoring of air pollutants is an essential issue in monitoring and studies of a variety of fields such as human heath, environmental protection, industrial development, protection of historical monument, sustainable development and nuclear chemical or biological emergency response. Thus along with development and progress of environmental protection technology, people's concepts and requirements of environmental protection, new techniques and patents are developed continuously. For example, refer to U.S. Pat. No. 5,040,424 "High volume PM.sub.10 sampling inlet", applied by Virgil A. Maple et al of the University of Minnesota in 1990, a sampling inlet removing the part of particles that are larger than 10 microns is revealed. Refer to U.S. Pat. No. 6,402,817 "Low pressure drop, multi-slit virtual impactor", applied by Werner Bergman et al of the University of California in 2000, an inertia of particles suspended in air flow is increased by increasing speed of the air flow. Once the particles having an inertia greater than a given amount (a threshold), the particles with sufficient inertia don't move along with the direction of the air flow, and will impact on the flat surface directly and will be trapped in the receiving chambers. The airstream is accelerated to different levels gradually so as to classify particles suspended in the air. Refer to Chinese Pub No. 1695771 "Sampler for aerosol granules", applied by Chen Xu et al of the Tsinghua University, this patent is also based on the inertia and impact. A plurality of particles with different aerodynamic diameters in air stream is collected and samples with sufficient amount and evenness are provided. Simultaneously, the stability of particles with various cut size are ensured. Moreover, refer to Chinese Pub. No. 1654944 "Radioactive aerosol granularity separating and sampling unit" applied by Lu Zhengyong et al, China Institute for Radiation Protection, utilizing the property that the size of RnTh daughter is smaller than the normal size of artificial aerosol to separate the natural and artificial nuclides. The interference to artificial airborne radioactivity measurement caused by RnTh could be reduced by the sampling unit. Refer to Taiwanese Pat. No. 1294034 "Sampling method for bio-aerosol in air", applied by Chin-Shin Lin of archilife research foundation in 2006, the bioaerosols in air such as allergens and fungus are sampled and analyzed for evaluating health risks. However, above prior arts are designed according to natures of the air pollutants.

Moreover, some inventions focus on progress of working forms. For example, refer to U.S. Pat. No. 6,167,766 "Programmable atmospheric sampling systems and method" applied by David L. Dunn et al. of Westinghouse Savannah River Company in 1997, a sampling system is revealed. The sampling system controller includes a control unit for management of a plurality of sampling chambers. Samples are acquired according to the timing and the flow rate controlled by program codes saved in a data module. Moreover, refer to Chinese Pub. No. 101231220 "passive atmospheric aerosol individual sampler" applied by Liu Wei et al. of Chinese Academy of Sciences in 2007, for individual research in microenvironment, a portable passive sampling apparatus different from conventional active sampling type and convenient for carrying is provided.

Furthermore, some other inventions put much emphasis on the integration of sample continuity and measurement instruments. For example, refer to Chinese Pub. No. 2884178 "A quick trap method for atmospheric particles" applied by Wang Yue-Si et al. of Chinese Academy of Sciences in 2007, all-weather sampling is achieved by membraneless sampling of suspended particles. Also refer to Chinese Pub. No. CN2856982 "Continuous sampling paper feeding integrated device for radioactive aerosol" applied by Zhang Zhilong et al. of China Institute of Radiation Protection in 2005, a continuous sampling paper feeding integrated device that can real-time monitor radioactive aerosol from nuclear facilities with increased utility and reliability is revealed.

Air samplers are divided into active type and passive type according to a control way of air flow that enters the sampler. The active type requires a power source (air pump) to withdraw the air and mostly takes samples at a fixed point. Thus the sample representativeness is lower. Although there are commercial portable air samplers available now, they are applied to monitoring of respiration of staffs. The sampling rate is close to respiration rate of staffs (2 L/min) so that it's not suitable for environmental air sampling (50 L/min). Once the active air sampler that requires power sources is loaded on a vehicle to perform air sampling at multiple locations with higher flexibility, the air sampling rate of air pump is affected by interference of gas turbulence generated during the movement of the vehicle. Thus the preset air sampling flow of the air pump is also affected and the volume of air samples is unable to be obtained correctly and precisely. Therefore, while performing air quality monitoring now, a plurality of air pumps is used to get air samples in a certain area. However, conventional active air sampling uses a air pump to take samples at a fixed point continuously and exhaust air at the same point. "The sampled air" can't be restricted and may be sampled again by the active air sampler. Thus the concentration of pollutants in the air samples will be diluted and then the sampling will loss the representativeness of samples.

Moreover, natural disaster surveys or emergency events that require environmental air sampling may occur at any position such as outdoors or city streets. Generally, most power for outdoor use is high voltage such as 380V power supply except special ones applied and obtained from electric power companies. Such a high voltage power supply is not suitable for a normal air pump to take air samples. In order to use outdoor powers, users need to prepare power converters. Thus it is difficult to get and inconvenient to use outdoor power sources. As to indoor power sources such as 110V, the power points are arranged inside the buildings so that the air pump is inconveniently connected with the power point by extension cords. Users have better to prepare generators for power supply of the air pump. Thus the conventional active air samplers are very labor and time consuming. It is disadvantageous to flexible sampling and the requirement of multi-point or wide area sampling is difficult to be satisfied. The passive-type air samplers depend on natural air circulation while its sampling rate is low and instability is high. Once the samplers are carried by staffs or moved along with vehicles, it's more difficult to estimate the sampled air volume. Such sampling way is suitable to long-term (over months, seasons and years) and static sampling works.

Thus the present invention designs an air pollution sampling system that uses a force generated by the movement of the vehicle as a power source to replace conventional air pumps so as to avoid trouble of the power source caused by the use of air pump. Without using power, the high flow active sampling is still achieved. Moreover, during the movement of the vehicle, the sampling flow of the flow meter and the sampling positions of the geographic positioning device are recorded automatically and precisely so as to achieve wide-area multi-point sampling and increase the representativeness of air samples. During the sampling period, the geographic positioning device such as GPS, INS/GPS, and INS/GPS/AHRS available can provide movement speed and even three-dimensional speed data of the vehicle. If there is an established correlation function between the air sampling flow rate and the vehicle speed, it could be input into a processing unit. The vehicle speed is converted into air sampling rate so that there is no need to use the flow meter. The cost for setting air pollutant samplers will be dramatically reduced. The air sampling point will be moved along with the vehicle so that the backflow and dilution problems of the air sampling taken at fixed points can be avoided. Once the vehicle stops moving, the air sampling will end immediately. The sample volume (or the sampling rate) along the sampling path distributes well and evenly on the area with the sampling points. And there is a special emphasis on that the air sampling system does not need to equipped with any air pump which can have large air sampling rate.

The samples are taken during the movement of the vehicle. The sampling system could be equipped with the vehicle before go into the sampling. The vehicle can be controlled remotely or driver, thus staffs responsible for air sampling don't need to set up the air pollution sampling system directly in the polluted environment and the risk of exposure to pollutants is reduced. Furthermore, an extended sample port and baffle plates are disposed in front of a filter so as to avoid interference cause by turbulence generated during the movement of the vehicle. However, the vehicle itself also disturbs the air surrounding. Thus the extended sample port is designed to avoid the air turbulence caused by the vehicle. In order to prevent rain drops or sands bumps from impact on the filter layer directly, the baffle plate is arranged in front of the sample port. The size and the angle of an opening of the sample port are adjustable to control air sampling flow. The sampling force of air relates to the movement speed of the vehicle and the positioning device can measure the vehicle speed. Thus even there is no flow meter, the sampling flow rate of air samples can be calculated according to the movement speed of the vehicle. The present invention further includes an information storage unit together with the geographic information system for data collection and integration so that the sample results can be used for following applications.

SUMMARY OF THE INVENTION

Therefore it is a primary object of the present invention to provide an air pollution sampling system that is loaded on a vehicle and a force generated by the movement of the vehicle is used as a power of a sampling device so as to avoid trouble caused by the use of power sources and provide a precise sampling volume.

It is another object of the present invention to provide an air pollution sampling system in which a baffle plate is disposed on an air inlet of an air sampling unit. The air sampling unit extends forward so as to avoid interference cause by turbulence generated during the movement of the vehicle. The size of an opening of the air sampling unit is controlled to adjust the air sampling rate. The baffle plate prevents interference from rain drops and coarse sands.

It is further object of the present invention to provide an air pollution sampling system that takes samples during movement of the vehicle to achieve wide-area multi-point air sampling.

It is further object of the present invention to provide an air pollution sampling system in which an information processing device integrates data of volume and sampling position of air samples and then the data is displayed on a geographic information system. Thus the area represented by multi-point wide-area environmental sampling is confirmed and the management of air sampling is achieved In order to achieve above objects, an air pollution sampling system according to the present invention uses a force generated by the movement of the vehicle as a power, instead of the power provided by conventional air pumps and takes samples during the moving period of the vehicle so as to achieve multi-point wide-area environmental sampling and increase the sample representativeness of the samples. Moreover, the turbulence caused by the vehicle, interference of rain and sand are avoided and the air sampling rate can be controlled.

The air pollution sampling system includes an air sampling unit, a flow estimation unit, a positioning device, and an information processing device. The air sampling unit includes an extended sample port unit for adjusting air sampling rate and preventing interference cause by turbulence generated during the movement of the vehicle, and a filter unit that changes filtering materials therein according to properties of air pollutants. The extended sample port unit includes a forward extending body that is a hollow chamber so as to make the sample port extend a certain length to avoiding turbulence flow caused by the vehicle. Thus the sampling flow rate becomes more stable. The extended sample port unit further has a baffle plate for removing rain drops and sands and an opening with adjustable size for control of the air sampling rate. The flow estimation unit could correct the results measured by instruments and converts the results into the required unit of air sampling rate. Generally, the instrument is a flow meter. The air sampling rate could be corrected according to the meter factor, atmosphere pressure, temperature and moisture. The positioning device can be a GPS, INS (inertial navigation system)/GPS INS/GPS/AHRS (Attitude Heading Reference System) or WiFi positioning that provides geographic coordinates, vehicles speed (two-dimensional or three-dimensional) and time. The information processing device consists of an information integration unit, an information storage unit, a processing control unit, and a wireless network unit. The information integration unit integrates information from the flow estimation unit and from the positioning device and then saves the data into the information storage unit. According to the commands, the processing control unit computes statistics of accumulated sampling amount and the area of the sampling position. Through the wireless network unit, the information processing device shows the air-sampling data to staffs or operation center. Moreover, a geographic information system could be directly connected with or is indirectly through the wireless network unit to connect with the information processing device for displaying and managing sampling positions. By the display of the geographic information system, the geographic area represented by the air samples could be understood clearly. When a new need to increase sampling positions comes, the vehicle could receive the command and then moves to the positions immediately. Therefore, a good and real-time sampling management could be achieved.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
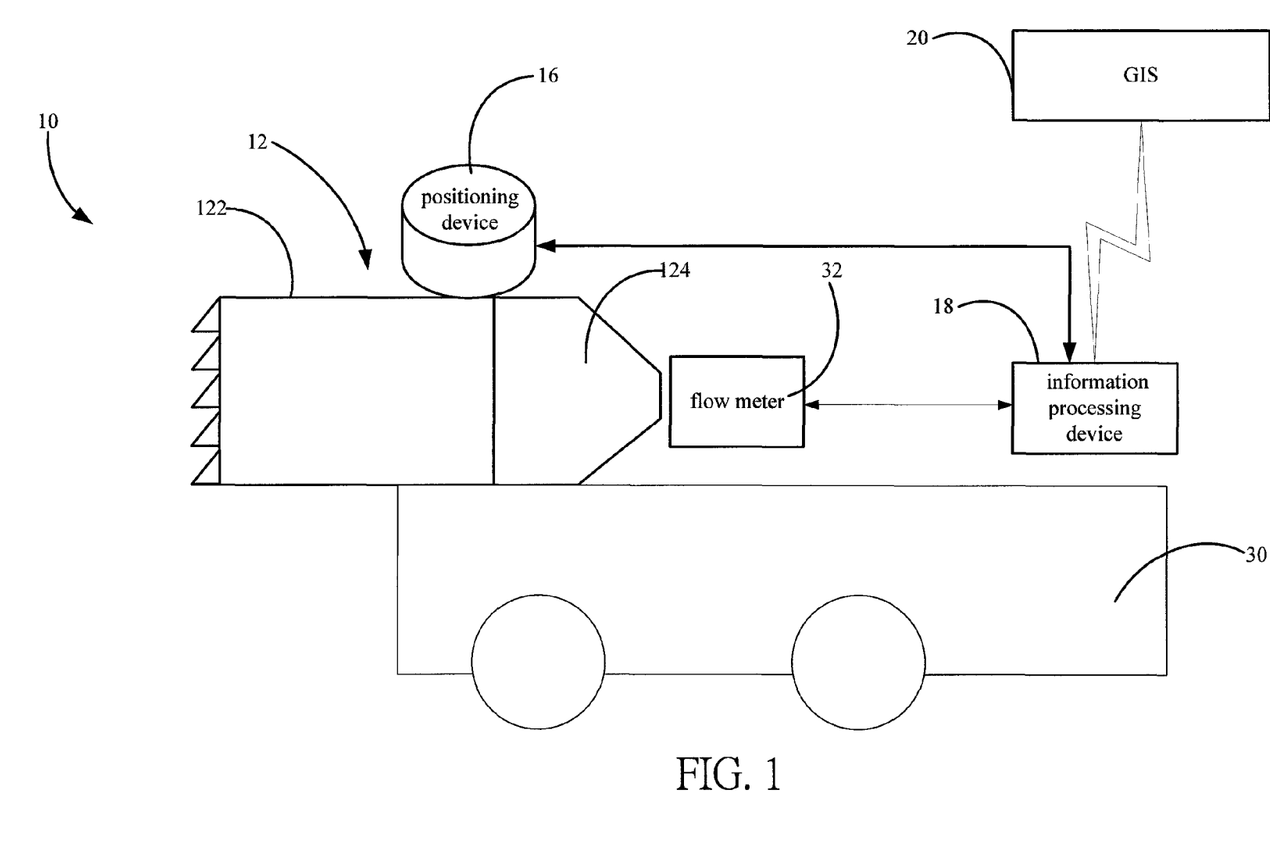
FIG. 1 is a block diagram showing structure of an embodiment according to the present invention.

Refer to FIG. 1, a block diagram of an embodiment according to the present invention is revealed. As shown in figure, an air pollution sampling system 10 of the present invention is loaded on a vehicle 30 that can be driven by human operators or by remote control and moving around in a sampling area. The vehicle could be a vehicle for moving on land, on water or in air. By a thrust generated during movement of the vehicles, air is pushed into an air sampling unit 12 of an air pollution sampling system 10. Thus active sampling without power is achieved. The sampling is stopped automatically when the vehicle stops (the speed is zero), without the use of a switch to control the beginning and the end of sampling. During the movement of the vehicle, a wide-area multi-point environmental sampling is achieved and the sampling volume of each sampling point (position) is more even. This helps to get a representative sample of the environmental air in the designated area. Moreover, due to continuous movement during sampling processes, the problem of conventional air sampling such as dilution of the target pollutants caused by the return air flow after the sample being filtered by the sampling filter can be avoided. The air sampling unit 12 is connected with a flow estimation unit 14. Air samples flowing from the air sampling unit 12 enter the flow estimation unit 14 to measure and calculate the volume of the air samples. At the same time, a positioning device 16 gets geographic coordinates. The measurement results of the volume of the air samples and the geographic coordinate data are integrated by an information processing device 18. Then the related data is sent to a geographic information system (GIS) 20 for display. Thus the designated area for multi-point wide-area environmental sampling is confirmed and the management of the air samples is achieved. The air sampling is finished precisely and accurately during the movement of the vehicle 30 so that people responsible for air sampling don't need to set up the air pollution sampling system directly in the environmental. Thus the risk of damage caused by air pollutants harmful to human health is reduced. This is especially helpful in protection of people responsible for environmental monitoring during chemical or nuclear accidents with highly concentrated pollutants or emergency response to incidents involving radiological/nuclear, biological and chemical terrorism.

Figure 2:
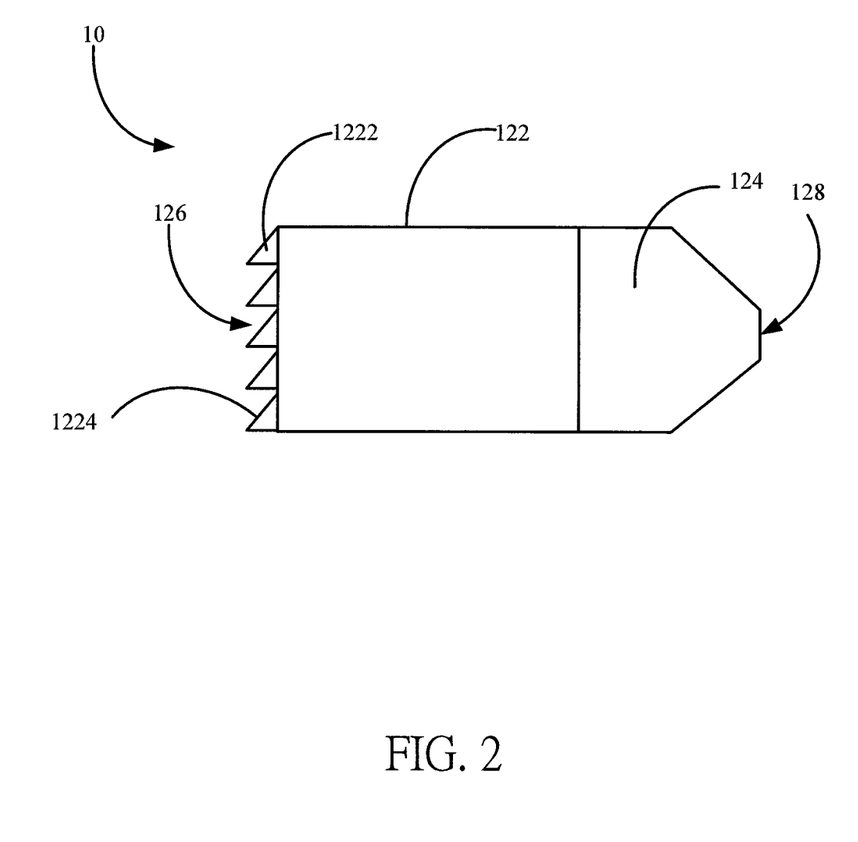
FIG. 2 is a schematic drawing showing an air sampling unit of an embodiment according to the present invention.

As shown in FIG. 2, the air sampling unit 12 includes an extended sample port unit 122 connected with a filter unit 124. The extended sample port unit 122 is used for guiding air flowing the air pollution sampling system 10. In order to prevent gas turbulence caused by the movement of the vehicle 30, the sampling port is extended forward by a forward extending body 1222 that is a hollow chamber with an opening on the front end thereof. The shape and the size of the opening on the front end are not limited. It can be a geometric pattern such as rectangular, round and so on and the size depends on the sampling target. The rear end of the extended sample port unit 122 is connected with the filter unit 124 firmly. The shapes and sizes of two ends of this hollow chamber are different so that the surface of the middle part of the housing for the hollow chamber needs to be smooth. Moreover, while sampling in the environment, there may be rains, suspended branches and leaves, or irrelevant sands and dust that collide with the filter unit 124. Thus a baffle plate unit 1224 extending forward is disposed on an air intake unit 126 arranged at the extended sample port unit 122. Generally, rain drops or sands are large particles with certain mass. The larger the mass, the larger the inertia. Thus the rain drops or sands are with certain inertia, not flowing along with the gas flow into the air intake unit 126, and are bumping into the baffle plate unit 1224 to be removed. At the same time, the air sample taken passes the filter unit 124 evenly. There is a plurality of baffle plate units 1224 as well as a plurality of air intakes 126 designed to be arranged at the extended sample port unit 122.

The air intake unit 126 is a moveable opening. The air sampling rate of the air intake unit 126 is controlled by control of the area of air inlet. The kinds of air pollution are quite complicated. The selection of filter systems used for capturing pollutant is depended on the target air pollutant. The filter unit 124 includes an opening for changing various filter systems. For example, air pollutants are captured by a filter system that includes a filter, an activated carbon layer, absorbents, or combinations of multiple filtering materials. In order to improve collection efficiency of pollutants and reduce air resistance, in a preferred embodiment of the present invention, the filter in the filter unit 124 is HEPA filter that removes at least 99.97% of airborne particles so as to get better samples and its low air resistance increases sampling air flow. After completion of the sampling, the filter materials are removed from the filter unit 24 for further pollutant analysis and replaced a new one for next sampling.

Figure 3:
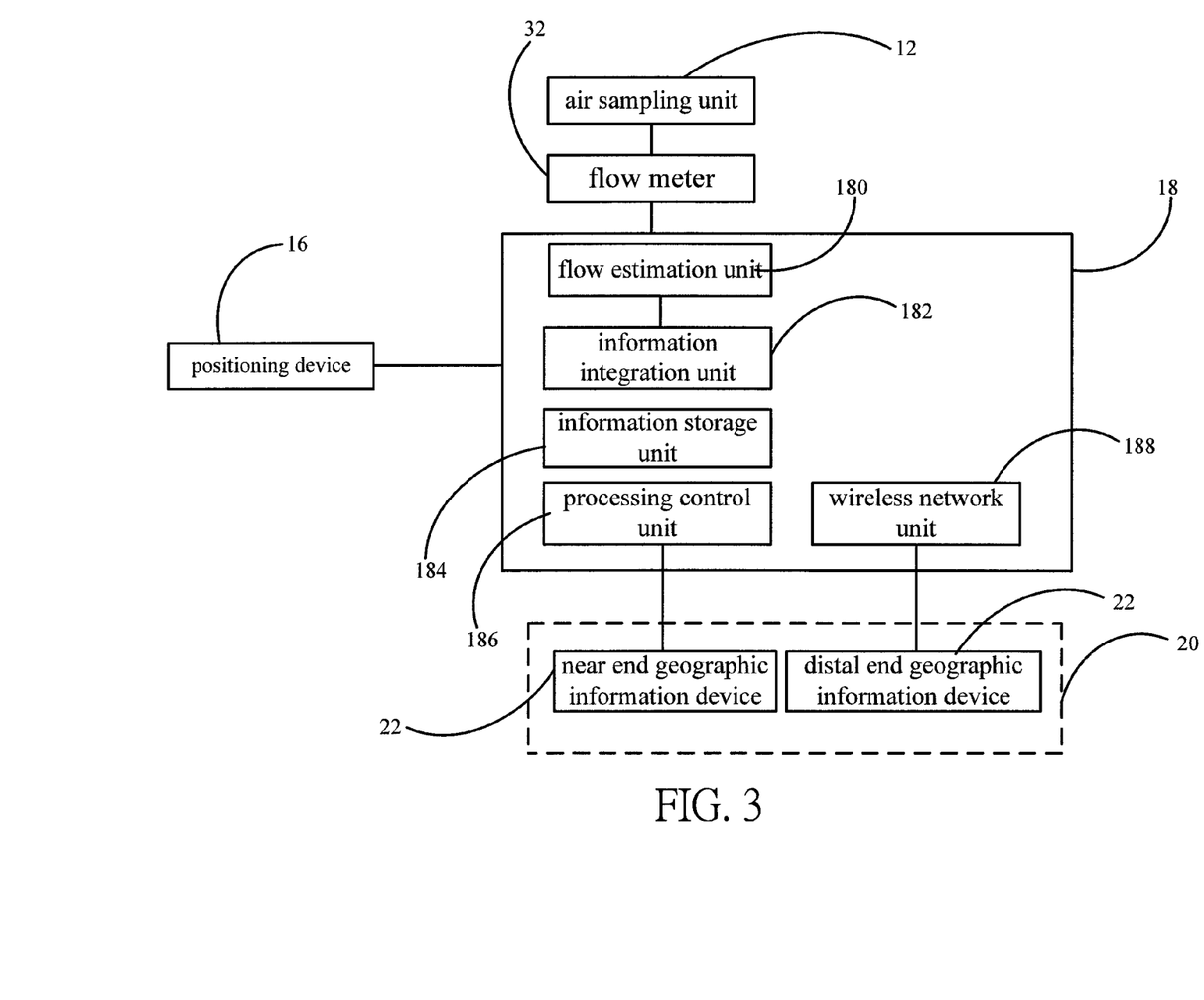
FIG. 3 is a block diagram of a sampling system of an embodiment according to the present invention.

Moreover, as shown in FIG. 3, the information processing device 18 of the present invention consists of a flow estimation unit 180, an information integration unit 182, an information storage unit 184, a processing control unit 186, a wireless network unit 188, and a geographic information system 20 having a near end geographic information device 22 and a distal end geographic information device 24. The flow estimation unit 180 is used to correct measured results of instruments and converts the results into the required unit for providing air sampling rate. The instrument is generally a flow meter 32. The air sampling rate is corrected according to the meter factor, atmosphere pressure, temperature and moisture. As to the information integration unit 182, it collects and integrates measured results of the flow meter 32 and of the positioning device 16 and then save the data into the information storage unit 184. According to the commands, the processing control unit 186 retrieves data regarding volume and relative position of the air sample from the information storage unit 184, gathers accumulated sample amount and estimates the area of the sampling position. Or it can also do conversion of unit for the sampled volume and the sampled rate. For example, convert "liter" into "cubic meter", "LPM (liters per minute)" into "cubic meter per second ($m^3/s$)". The results are displayed on the geographic information system 20. The near end geographic information device 22 is directly connected with the information processing device 18 to display the results while the distal end geographic information device 24 shows the real-time results through the wireless network unit 188. Thus even staff and experts not directly assigned to the sampling site can learn the geographic region that the air sample represents. Generally, environmental sampling takes much time and labor. The real-time display of the positions, volume and distribution of samples by the application of the geographic information system 20 enables users to check whether the air samples available now are enough to meet their requirements quickly by visualizing the data. Once the users find the covered area or the volume of the sample is not sufficient or other deficiencies, they can make compensation immediately. Thus the labor and resources for sampling are saved and better sampling timing is achieved.

Figure 4:
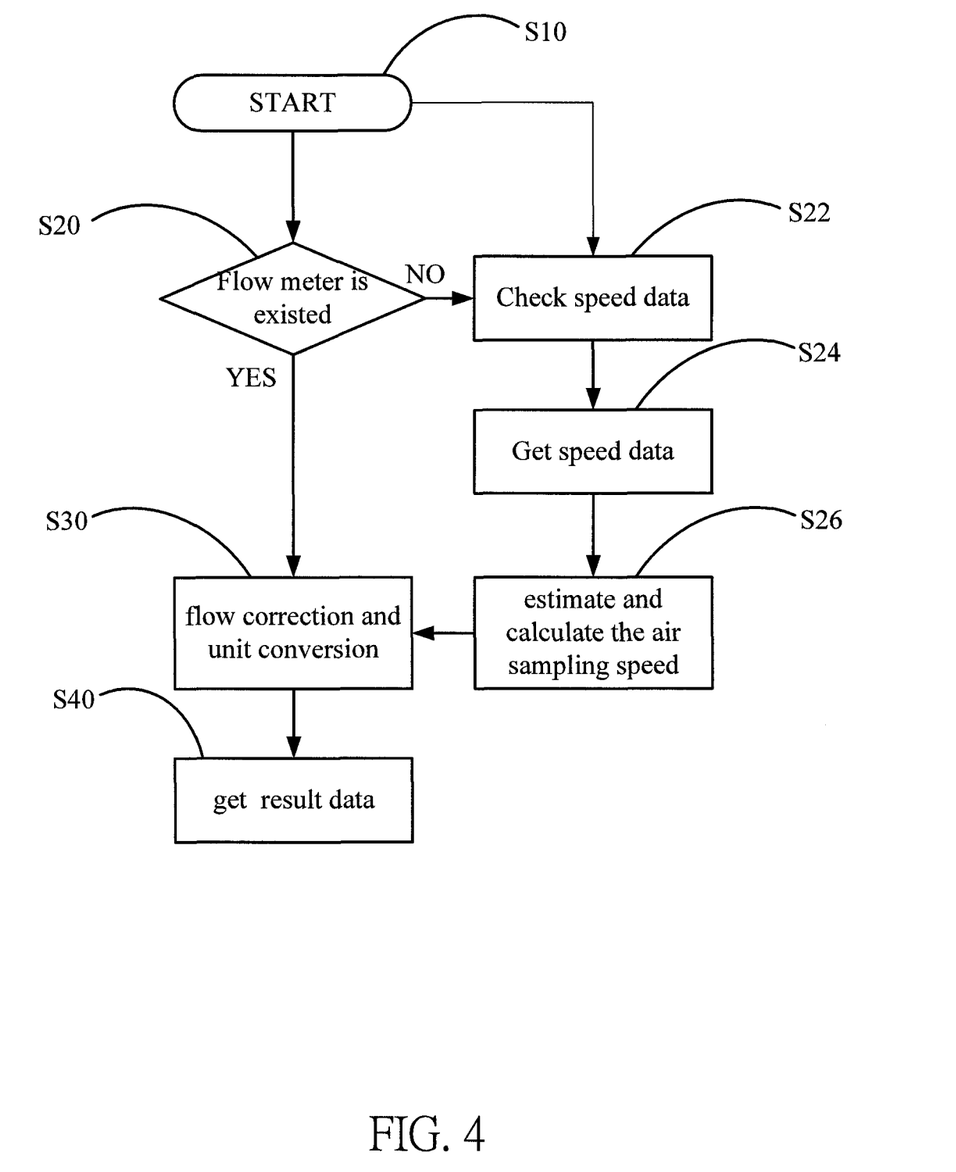
FIG. 4 is a flow chart of a sampling method of an embodiment according to the present invention.
Figure 5:
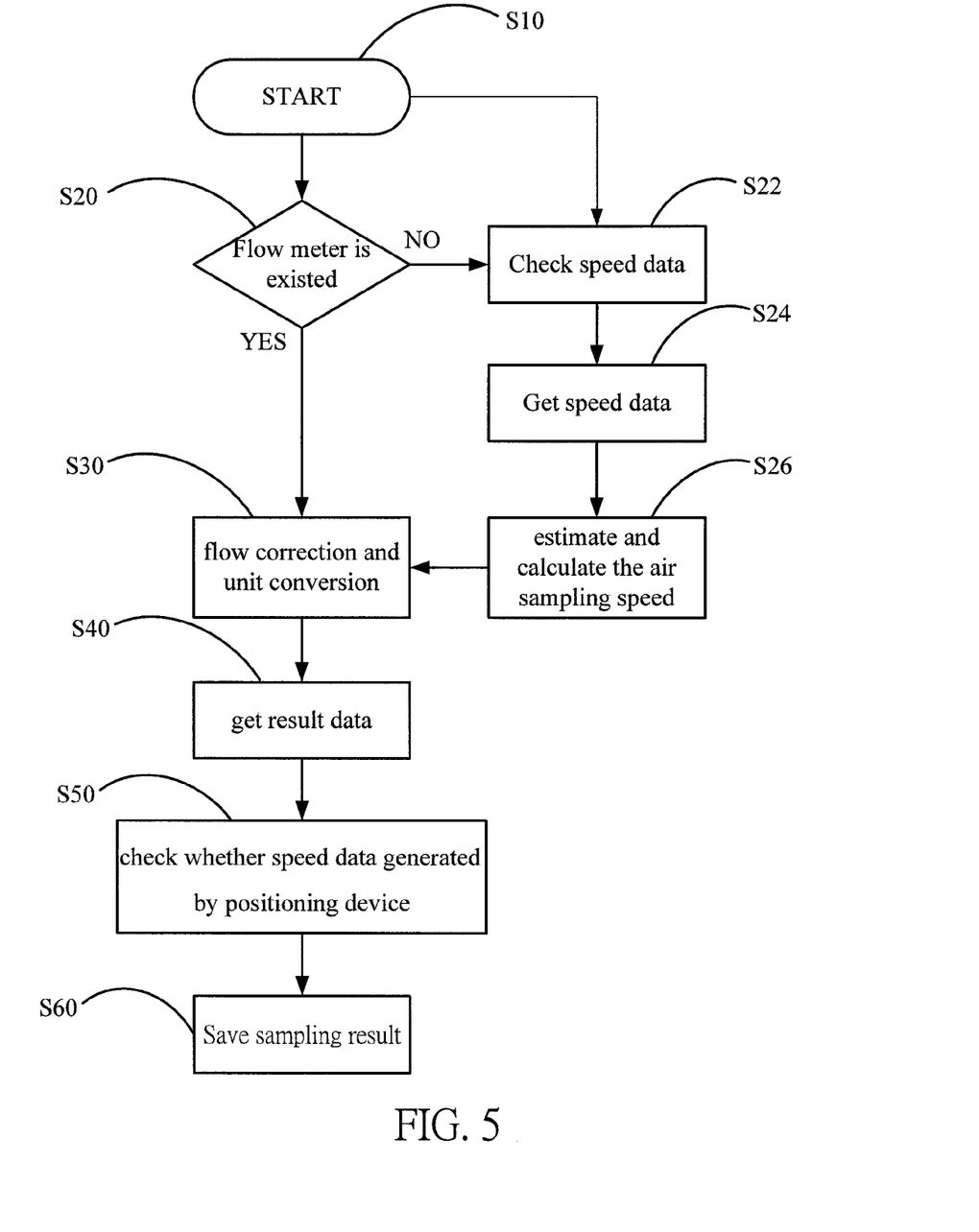
FIG. 5 is a flow chart of a sampling method of another embodiment according to the present invention.

Besides measured by the flow meter 32, the air sampling rate can also be estimated by the flow estimation unit 180 according to a correlation function between a vehicle speed obtained from the positioning device 16 and air sampling rate. The flow chart and related details are shown in FIG. 4. A sampling method of the present invention is revealed in FIG. 4. As show in FIG. 4, the sampling system of the present invention runs the step S10 when the vehicle 30 starts moving and the information processing device 18 is turned on. When the vehicle 30 moves forward, air flow into the air sampling unit 12 and the information processing device 18 is simultaneously turned on. Next take the step S20, the flow estimation unit 180 firstly checks whether the information processing device 18 is connected with the flow meter 32 for measurement of the sampling flow of the air sampling unit 12. Once the information processing 18 is connected with the flow meter 32, it receives measured data from the flow meter 32, run the step S30, and execute flow correction and unit conversion by means of flow correction factor of the flow meter 32 and unit conversion factor saved in the information storage unit 184. Then as shown in the step S40, a result data of air pollution sampling rate is obtained. Back to the step S20, if the flow estimation unit 180 finds that there is no flow meter 32, it takes the step S22. Check whether the positioning device 16 has the speed data by the information integration unit 182. If the answer is yes, run the step S24, get the speed data. Then as shown in the step S26, estimate and calculate the air sampling rate through conversion of the speed and the flow by the correlation function between the vehicle speed and the air sampling rate established in the flow estimation unit 180. Next take the step S30, execute flow correction and unit conversion. As shown in the step S40, get the result data of the sampling rate. Moreover, refer to FIG. 5, the sampling method of the present invention further includes a step S50, by the processing control unit, check whether the speed data generated by the positioning device 16 according to the movement speed of the vehicle 30 is used to get the result data of the sampling rate. If yes, run the step S60 while if not, run the step S20, get the result data of the sampling rate again. As shown in the step S60, the result data of the sampling rate obtained in the step S40 is integrated with the geographic location data generated from the positioning device 16 by the information integration unit 182 and then saved into the information storage unit 184.

In summary, the air pollution sampling system of the present invention has the following advantages:
1. Without use of a air pump or a blower, the air pollution sampling system can still achieve high flow rate sampling.
2. The sampling rate and volume measurement of the air pollution sampling system are precise and accurate. These data can also used in combination with positioning device and sampling position acquired by the GIS and the sampling results are recorded precisely and accurately. This favors following analysis and reports.
3. The air pollution sampling system can take samples during movement of the vehicle and each place is considered as a sampling point. The movement path of the vehicle passes a plurality of sampling points so as to achieve multi-point sampling. The sampled results of the air samples are local sampling results so as to increase the sample representativeness.
4. The air pollution sampling system moves along with the vehicle to pass the air sampling points. Thus the backflow problem of the air sampling by the sampling system at a fixed point will not occur. Once the vehicle stops, the sampling pauses/stops. The switch problem of air pump is not needed to worry.
5. The air pollution sampling system takes samples during the movement of the vehicle. Thus no matter the vehicle is controlled remotely or driven by people, staffs responsible for air sampling don't need to set up the air pollution sampling system directly in the polluted environment and the risks of health and life caused by pollutants are reduced.
6. By the extended sample port, air is guided to enter the air inlet so as to avoid the air turbulence caused by the movement of the vehicle and having effects on the flow.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. An air pollution sampling system for being loaded on a vehicle, comprising:
    an air sampling unit disposed on the vehicle and having a plurality of baffle plates for guiding air entering the air sampling unit during movement of the vehicle;
    a positioning device for positioning the vehicle, providing a geographical position of the vehicle and generating a positioning information correspondingly, and providing a movement speed of the vehicle; and
    an information processing device connected with the positioning device, calculating a sampling flow of the air sampling unit according to the movement speed and recording a sampling area corresponding to the sampling flow according to the positioning information, wherein air pollutant samples are collected for analysis.
2. The system as claimed in claim 1, wherein the air sampling unit includes:
    a chamber having an air inlet and an air outlet, and the chamber disposed on the vehicle;
    a plurality of forward extending bodies disposed on the air inlet and each forward extending body having a baffle plate for guiding air into the air inlet during a movement of the vehicle while the air entering the chamber is exhausted from the air outlet; and
    a filter unit arranged at the chamber, filtering the air entering the chamber and taking air samples.
3. The system as claimed in claim 2, wherein the air pollution sampling system further includes:
    a flow meter that connects with the filter unit and the information processing device; the flow meter measures air flow of the air sampling unit to generate a measured value of the sampling flow and send the measured value of the sampling flow to the information processing device; then the information processing device corrects the sampling flow according to the measured value of the sampling flow.
4. The system as claimed in claim 2, wherein the air inlet as well as the air outlet is a geometric shape.
5. The system as claimed in claim 2, wherein the filter unit includes an activated carbon layer.

6. The system as claimed in claim 2, wherein the filter unit includes a layer of High Efficiency Particulate Air (HEPA) filter.

7. The system as claimed in claim 2, wherein an air flow rate of the filter unit is corresponding to a movement speed of the vehicle.

8. The system as claimed in claim 1, wherein the information processing device comprising:
- a flow estimation unit connected with the air sampling unit and the positioning device, calculating the sampling flow of the air sampling unit according to the movement speed, and computing statistic of a sampling result of the filter unit;
- an information integration unit connected with the flow estimation unit and the positioning device, and generating a result data of sampling speed according to the sampling result, a flow of the air and the positioning information; and
- an information storage unit that connected with the information integration unit, saves and updates the result data of the sampling rate according to the positioning information.

9. The system as claimed in claim 8, wherein the information storage further saves at least one movement path of the vehicle and the vehicle moves according to the movement path.

10. The system as claimed in claim 9, wherein the air pollution sampling system further includes:
- a processing control unit connected with the information storage unit; and
- a geographic information system (GIS) connected with the processing control unit and the processing control unit updates the movement path saved in the information storage unit according to the geographic information system.

11. The system as claimed in claim 8, wherein the air pollution sampling system further includes:
- a processing control unit connected with the information storage unit; and
- a geographic information system connected with the processing control unit and the processing control unit uploads the result data of sampling rate to the geographic information system according to the information storage unit.

12. The system as claimed in claim 11, wherein the processing control unit is a central processing unit, a digital signal processing unit or an application-specific integrated circuit (ASIC).

13. The system as claimed in claim 1, wherein the positioning device is a global positioning system (GPS) or an inertia navigation system (INS).

14. An air sampling method for an air pollution sampling system arranged at a vehicle, comprising the steps of:
- using an air sampling unit to takes air samples during movement of the vehicle and air entering the air sampling unit during the movement of the vehicle;
- positioning the vehicle and generating a positioning information correspondingly;
- retrieving a movement speed of the vehicle;
- calculating a sampling flow according to the movement speed; and
- recording a sampling area corresponding to the sampling flow according to the positioning information, wherein air pollutant samples are collected for analysis.

15. The method as claimed in claim 14, wherein before the step of calculating a sampling flow according to the movement speed, the method further includes steps of:
- checking whether a flow meter exists; run the step of retrieving a movement speed of the vehicle directly if the flow meter doesn't exist;
- retrieving a measured value of the sampling flow by the flow meter if the flow meter exists.

16. The method as claimed in claim 15, wherein after the step of calculating a sampling flow according to the movement speed, the method further includes a step of:
- correcting the sampling flow according to the measured value of the sampling flow.

17. The method as claimed in claim 14, wherein after the step of recording a sampling area corresponding to the sampling flow according to the positioning information, the method further includes steps of:
- getting a result data of sampling rate according to the movement speed; and saving the result data of sampling rate

* * * * *